(12) United States Patent  
Finter et al.

(10) Patent No.: US 9,157,015 B2
(45) Date of Patent: Oct. 13, 2015

(54) CONDENSATION PRODUCTS OF AMINO-FUNCTIONAL POLYMERS

(75) Inventors: Juergen Finter, Zurich (CH); Ulrich Gerber, Uitikon-Waldegg (CH); Edis Kasemi, Zurich (CH); Andreas Kramer, Zurich (CH)

(73) Assignee: SIKA TECHNOLOGY AG, Baar (CH)

( * ) Notice: Subject to any disclaimer, the term of this patent is extended or adjusted under 35 U.S.C. 154(b) by 0 days.

(21) Appl. No.: 13/882,681

(22) PCT Filed: Nov. 10, 2011

(86) PCT No.: PCT/EP2011/069838
§ 371 (c)(1),
(2), (4) Date: Apr. 30, 2013

(87) PCT Pub. No.: WO2012/062853
PCT Pub. Date: May 18, 2012

(65) Prior Publication Data
US 2013/0225723 A1 Aug. 29, 2013

(30) Foreign Application Priority Data
Nov. 11, 2010 (EP) .................................. 10190823

(51) Int. Cl.
| C08L 63/00 | (2006.01) |
| C09D 163/00 | (2006.01) |
| C09J 163/00 | (2006.01) |
| C08G 59/40 | (2006.01) |
| C08G 59/64 | (2006.01) |
| C08G 65/26 | (2006.01) |
| C09J 11/08 | (2006.01) |

(52) U.S. Cl.
CPC ............. *C09J 11/08* (2013.01); *C08G 65/2612* (2013.01); *C08L 63/00* (2013.01); *C09D 163/00* (2013.01); *C09J 163/00* (2013.01)

(58) Field of Classification Search
USPC .......................................................... 528/162
See application file for complete search history.

(56) References Cited

U.S. PATENT DOCUMENTS

| 2,356,151 | A | * | 8/1944 | Eastes ............................ 521/39 |
| 3,462,393 | A | | 8/1969 | Legler |
| 3,734,965 | A | * | 5/1973 | Becker ........................ 564/367 |
| 5,098,986 | A | * | 3/1992 | Speranza et al. ............. 528/149 |
| 5,120,817 | A | * | 6/1992 | Speranza et al. ............... 528/99 |
| 6,262,148 | B1 | | 7/2001 | Cheng et al. |

FOREIGN PATENT DOCUMENTS

| EP | 0 253 339 A2 | 1/1988 |
| EP | 0 292 701 A2 | 11/1988 |

(Continued)

OTHER PUBLICATIONS

International Preliminary Report on Patentability issued in International Patent Application No. PCT/EP2011/069838 dated May 14, 2013.

(Continued)

*Primary Examiner* — Mark Kaucher
*Assistant Examiner* — Kregg Brooks
(74) *Attorney, Agent, or Firm* — Oliff PLC

(57) ABSTRACT

A condensation product of at least one (hydroxymethyl)phenol and at least one polyoxyalkylene diamine and a process for the preparation thereof and the use thereof in the curing of epoxy resin systems are described.

8 Claims, 3 Drawing Sheets

(56) References Cited

FOREIGN PATENT DOCUMENTS

| | | | |
|---|---|---|---|
| EP | 1 475 411 | A1 | 11/2004 |
| EP | 1 475 412 | A1 | 11/2004 |
| WO | WO 00/15687 | A1 | 3/2000 |
| WO | WO 2009/051699 | A1 | 4/2009 |

OTHER PUBLICATIONS

International Search Report issued in International Patent Application No. PCT/EP2011/069838 dated Apr. 20, 2012 (w/translation).

* cited by examiner

CONDENSATION PRODUCTS OF AMINO-FUNCTIONAL POLYMERS

The present invention relates to novel Mannich-like condensation products and a new process for the preparation thereof. Another subject of the present invention is the use of said condensation products as accelerators in the curing of one- and two-component epoxy resin adhesives.

DESCRIPTION OF THE BACKGROUND ART

An epoxy resin consists of polyether polymers, which depending on the reaction route with the addition of suitable hardeners produce a thermosetting plastic of high strength and chemical resistance. If epoxy resin and hardener are combined, the curing of the originally viscous mixture occurs typically within a few minutes to a few hours depending on the composition and temperature. Different systems are commercially available as hardeners for epoxy resins such as, for example, hardeners on an amine, amide, and anhydride base (for example, under the name Epikure® from Hexion Specialty Chemicals) or hardeners based on polyether amines (for example, under the name Jeffamine® from Huntsman).

Mannich bases of primary amines, formaldehyde, and phenols can also be used as hardeners or accelerators (cf., for example, EP 0 253 339 A). Further, WO 00/15687 also describes a Mannich base accelerator, which is prepared by transamination of a Mannich base with an amine.

A disadvantage of relevant customary Mannich bases is the use of phenol as a starting material, because the obtained Mannich bases often comprise not yet reacted phenol. Because of the toxicity of free phenol, phenol-based Mannich bases therefore cannot be used for many fields of application. For this reason, a great effort has been made to produce phenol-free Mannich bases. Thus, for example, Mannich bases based on nonylphenol or p-tert-butylphenol or cardanol were developed (cf. U.S. Pat. No. 6,262,148). Appropriate commercial products, such as Aradur® 3442 from Huntsman Advanced Materials Inc are also known.

A further disadvantage with the use of customary Mannich bases is that these are prepared with use of formaldehyde. Formaldehyde is implicated, inter alia, in the development of allergies and irritation of the skin, respiratory tract, and eyes. There is a need accordingly to provide Mannich-like condensation products that can be prepared without use of formaldehyde.

Another major disadvantage of known customary Mannich hardeners is the high viscosity, arising during their preparation because of the formation of oligomers and secondary products. Thus, high-molecular-weight and relatively high-viscosity resoles form by the reaction of phenols with formaldehyde in a customary Mannich base synthesis under basic conditions. If these high-molecular-weight and relatively high-viscosity resoles are to be reacted, for example, with polymeric polyamines, which per se also have a higher viscosity, to form customary Mannich bases, this generally does not succeed because of the high viscosity of the resulting reaction mixture. Therefore, customary Mannich bases of phenols, formaldehyde, and polymeric polyamines are generally not obtainable.

During the preparation of customary Mannich base hardeners, a large excess of amine is typically used to keep the molecular weight and thus the viscosity low. Therefore, customary Mannich base hardeners are generally used in a mixture with typical polyamines. The admixing of additional polyamines, however, mostly has a negative effect on the properties of the cured epoxy resin composition.

Moreover, the processes for preparing known Mannich bases are very costly and difficult to run, particularly when the formation of high-molecular-weight condensation products is to be prevented if possible. Thus, for example, EP 1 475 411 A discloses a two-stage process for preparing Mannich bases based on m-cresol or 3,5-xylenol and polyamines, in which preferably a tertiary amine is used. Likewise, a two-stage process for preparing Mannich bases is disclosed in EP 1 475 412 A, whereby these are obtained from phenols such as m-cresol, 3,5-xylenol, or resorcinol with polyamines, preferably with the use of tertiary amines. Such two-stage processes are associated with additional expenditures and increase the cost of preparing Mannich bases.

Proceeding from this state of the art, the object of the present invention is to provide alternative accelerators for epoxy resins or hardeners for epoxy resins and polyurethanes, which preferably do not possess the present disadvantages.

The object of the present invention in particular is to provide accelerators for epoxy resins or hardeners for epoxy resins and polyurethanes, which contain no free phenol.

The object of the present invention further is to provide accelerators for epoxy resins or hardeners for epoxy resins and polyurethanes, which contain no free formaldehyde.

Preferably, the use of phenols and formaldehyde should therefore be dispensed with in the preparation of the pertinent accelerators.

Furthermore, the object of the present invention in particular is to provide accelerators for epoxy resins or hardeners for epoxy resins and polyurethanes, which have no oligomeric byproducts.

Therefore, the accelerators should be obtainable in a simple manner without the formation of unwanted high-molecular-weight condensation products.

DESCRIPTION OF THE INVENTION

Figure 1:
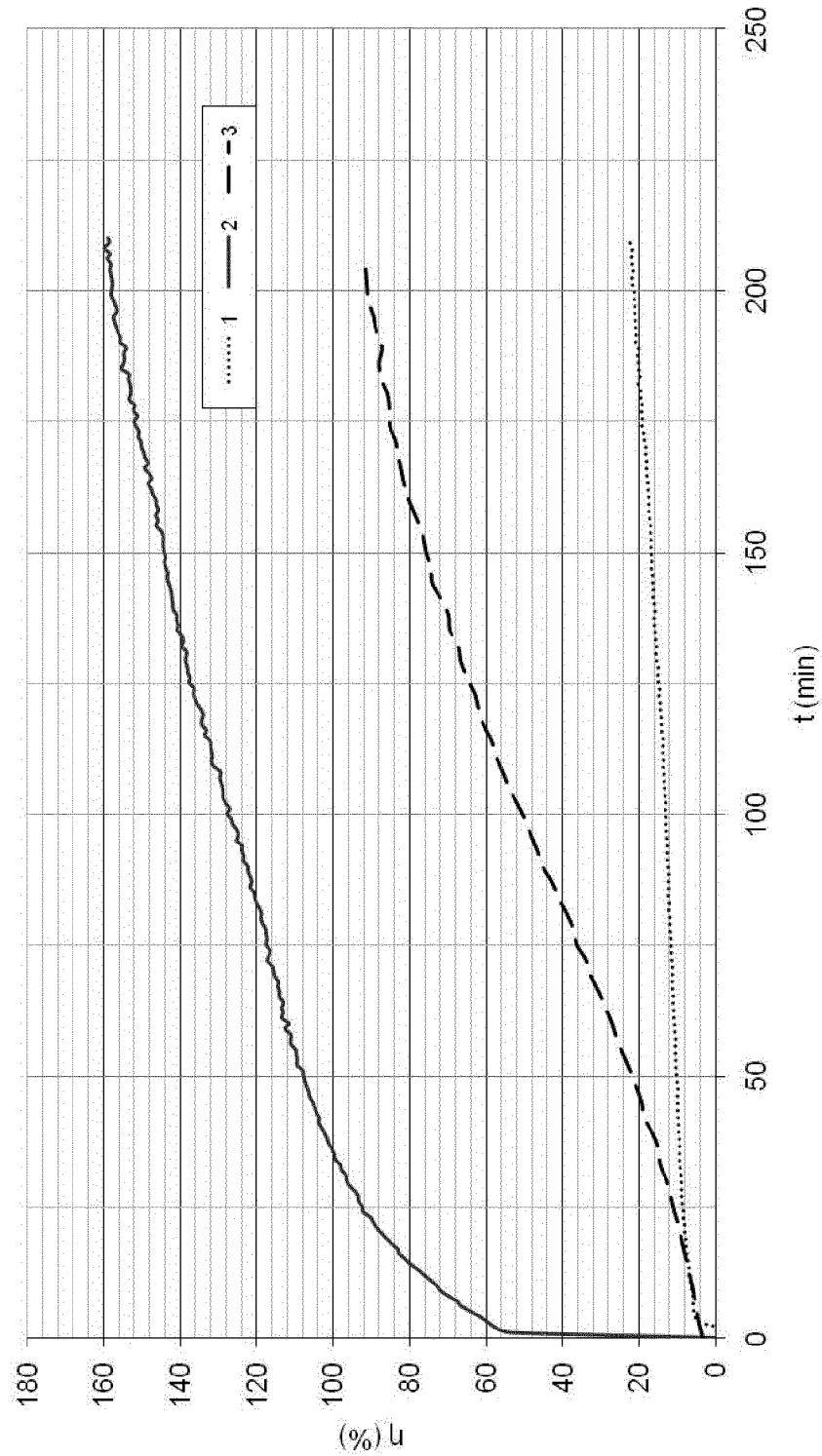
FIG. 1 is a graphical representation illustrating the relative increase in viscosity as a function of the reaction time for condensation product A.

Said objects are attained by a condensation product, which is formed from at least one (hydroxymethyl)phenol of the general formula (I)

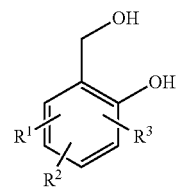

wherein:
$R^1$ is hydrogen or —$CH_3$;
$R^2$ is hydrogen or —$CH_2OH$; and
$R^3$ is hydrogen or —$CH_3$,
and at least one polyoxyalkylene diamine.

The condensation products of the invention are suitable as accelerators for epoxy resins and as hardeners for epoxy resins or polyurethanes.

In particular, these condensation products of the invention are suitable for accelerating the curing of epoxy resin adhesives and for improving the adhesion of epoxy resin adhesives and/or the peel strength of epoxy resin adhesives, whereby because of the use of special phenol and amine components the disadvantages known from the state of the art are substantially prevented. In particular, the condensation product of the invention comprises no free phenol and no oligomeric byproducts.

Because in contrast to the customary Mannich base synthesis the use of formaldehyde is avoided within the scope of the present invention, the resulting condensation products of the invention are also free of formaldehyde.

The condensation products of the invention are obtainable from readily available and cost-effective raw materials via a simple production process, which will be described in greater detail below and is also a subject matter of the present invention. The condensation products of the invention are notable particularly for excellent hardening behavior of epoxy resin adhesives.

Preferred embodiments of the condensation product of the invention will be described in greater detail below.

The present invention relates to a condensation product, which is prepared from at least one (hydroxymethyl)phenol as component (A) and at least one polyoxyalkylene diamine as component (B).

Convenient (A)—(Hydromethyl)Phenol

A (hydroxymethyl)phenol within the context of the present invention is understood to be an aromatic phenol, which has at least one methylol substituent in the ortho, meta, or para position to the phenolic OH group. Such phenols are obtainable commercially.

Within the context of the present invention, the phenols may have preferably one or two methylol groups. Preferably, the phenols have only one methylol group. Suitable examples are 2-(hydroxymethyl)phenol (salicylic alcohol), 3-(hydroxymethyl)phenol, 4-(hydroxymethyl)phenol, and 2,6-di(hydroxymethyl)-4-methylphenol. Especially preferred are 2-(hydroxymethyl)phenol (salicylic alcohol), 3-(hydroxymethyl)phenol, and 4-(hydroxymethyl)phenol.

The (hydroxymethyl)phenol used in the condensation product of the invention is a phenol which is substituted with a methylol group in the ortho position and optionally has other substituents, and corresponds to the general formula (I)

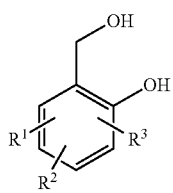

wherein:
$R^1$ is hydrogen or —$CH_3$;
$R^2$ is hydrogen or —$CH_2OH$; and
$R^3$ is hydrogen or —$CH_3$.

Preferably, $R^2$ is hydrogen. The condensation products prepared therefrom are distinguished by improved curing acceleration in epoxy resin compositions. Of course, mixtures of such (hydroxymethyl)phenols may also be used within the context of the present inventions for preparing condensation products of the invention.

The selection of the employed (hydroxymethyl)phenols greatly influences the properties of the resulting condensation products and thereby the epoxy systems resulting with the use of these condensation products as hardeners or accelerators.

Component (B)—Polyoxyalkylene Diamine

The condensation product of the invention is formed further from at least one polyoxyalkylene diamine. Within the context of the present invention, a polyoxyalkylene diamine is understood to be a compound that has terminally in each case two primary amine functions, which are connected by a polyoxyalkylene backbone.

The polyoxyalkylene diamine used in the condensation product of the invention preferably has units based on propylene oxide or ethylene oxide and propylene oxide.

It is preferable, furthermore, if the polyoxyalkylene diamine has a molecular weight in a range of 220 to 10,000 g/mol.

In a first embodiment of the present invention, the polyoxyalkylene diamine has the general structure (II)

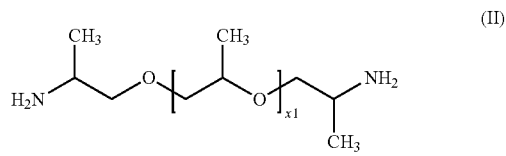

(II)

wherein X1 stands for a value of 2 to 70.

Suitable polyoxyalkylene diamines are commercial obtainable from Huntsman under the names Jeffamine® D-230, D-400, D-2000, and D-4000 with different proportions of propylene glycol units.

In another embodiment of the present invention, the polyoxyalkylene diamine has the general structure (III):

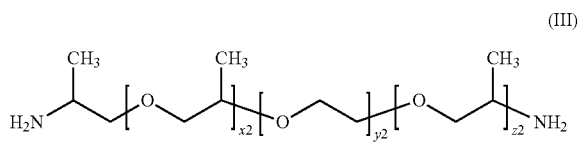

(III)

wherein the subscripts x2, y2, and z2 have the following meaning:
y2 is 2 to 40 and
x2+z2 is 1 to 7.

Suitable polyoxyalkylene diamines are commercial obtainable from Huntsman under the names Jeffamine® HK-511 (y2=2; x2+z2=~1.2); ED-600 (y2=~9; x2+z2=~3.6); ED-900 (y2=~12.5; x2+z2=~6.0), and ED-2003 (y2=~39; x2+z2=~6.0).

The condensation products of the invention of (hydroxymethyl)phenols and polyoxyalkylene diamines can be prepared from the previously described phenolic compounds and polyoxyalkylene diamines by a condensation reaction. The preparation of these condensation products is possible with use of customary condensation processes. Preferably, however, the condensation products are prepared by the process described below:

Thus, another aspect of the present invention is to new process for preparing the condensation products of the invention. This preparation process of the invention is distinguished in that at least one (hydroxymethyl)phenol is reacted with at least one polyoxyalkylene diamine.

A (hydroxymethyl)phenol compound as described above can be used as to (hydroxymethyl)phenol. In this respect, reference is made to the above statements.

A polyoxyalkylene diamine compound as described above can be used as to polyoxyalkylene diamine. In this respect, reference is also made to the above statements.

In a preferred embodiment, the process of the invention comprises the following process steps:
(i) Introducing at least one (hydroxymethyl)phenol and at least one polyoxyalkylene diamine at a temperature of 15 to 100° C., preferably 20 to 90° C., especially preferably 20 to 70° C., into a reaction vessel;
(ii) Raising the temperature to 120 to 190° C., preferably 120 to 180° C., especially preferably 120 to 170"C.

The reaction in the process of the invention, particularly the previously described process step (ii), is preferably carried out for a time period of 1 to 10 hours, preferably 1 to 8 hours, especially preferably 2 to 5 hours.

It is preferred, furthermore, if the process of the invention is carried out under inert conditions, particularly in the presence of an inert gas.

Advantageously, the at least one (hydroxymethyl)phenol is reacted with the at least one polyoxyalkylene diamine in a stoichiometric ratio of 1 to 30, preferably 1 to 10, especially preferably 1 to 1.

The present invention relates further to a condensation product, which can be obtained by the previously described process.

The condensation product of the invention is particularly suitable as a hardener for an amine-reactive substance, which has at least two amine-reactive functional groups. Glycidyl ether groups and/or isocyanate groups in particular may be used as such amine-reactive functional groups.

In an embodiment of the present invention, the amine-reactive substance, which has at least two amine-reactive functional groups is a diglycidyl ether. In particular, it is a diglycidyl ether of bisphenol A, bisphenol F, or bisphenol A/F. Such diglycidyl ethers are obtainable, for example, as Araldite® GY 250, Araldite® PY 304, Araldite® GY 282 (Huntsman), or D.E.R.™ 331 or D.E.R.™ 330 (Dow) or Epikote 828 (Hexion).

When the amine-reactive substance, which has at least two amine-reactive functional groups, is combined with the condensation product of the invention, a reaction of the amine groups of the condensation product with the amine-reactive functional groups of the amine-reactive substance occurs and curing takes place.

Therefore, the present invention relates particularly to the use of at least one condensation product of the invention or at least one condensation product, obtainable according to the above-described process, in epoxy resin systems, for example, within the scope of epoxy resin adhesives and coatings based on epoxy resins.

In particular, the condensation products of the invention are used for accelerating the curing of epoxy resin adhesives and improving the adhesion of epoxy resin adhesives and/or peel strength of epoxy resin adhesives.

The condensation product of the invention can be used as such or in a mixture.

The condensation products of the invention and the condensation products of the invention resulting from the process of the invention are used especially in hardener components of two-component epoxy systems. The condensation products of the invention can be used here directly or as constituents of the hardener components.

The condensation products of the invention are employed especially preferably as hardeners in two-component epoxy resin adhesives.

The two-component epoxy systems cured with these condensation products of the invention and the products obtained therefrom have very advantageous properties.

If the condensation product of the invention is employed for curing amine-reactive systems, the present invention also relates to a two-component composition, which consists of a first component K1 and a second component K2. The first component K1 comprises at least one amine-reactive compound having at least two functional groups which can react with amines. The second component K2 comprises at least one condensation product of the invention. Amine-reactive compounds, which have at least two functional groups that can react with amines, have already been described above.

Both components K1 and K2 can comprise as required other ingredients known to the person skilled in the art. Such additional ingredients are particularly fillers, softeners, solvents, catalysts, and/or additives.

Particularly preferred as fillers are carbon black, chalk, particularly coated chalk, sand, silicates, lightweight fillers, such as ceramic or glass beads, particularly hollow ceramic or glass beads, pyrogenic silicic acids, and fly ash.

Preferred as solvents are particularly those solvents that are not classified as VOC (volatile organic compounds). Especially preferred are higher-boiling hydrocarbons.

Phthalates and adipates, particularly diisodecyl phthalate (DIDP) and dioctyl adipate (DOA), are preferred as softeners.

Such two-component compositions can be used widely. Especially preferred is their use as an adhesive or sealant, particularly as a structural adhesive. It has been shown namely that the properties achievable by means the condensation products of the invention are especially desirable, particularly in the adhesive sector.

After components K1 and K2 of the described two-component composition are combined, the adhesive is applied to a substrate surface and joined to another substrate surface. The cured composition acts as an adhesive layer, which is capable of transferring forces between the two substrate surfaces of the formed composite body.

The two-component composition because of its properties is especially well suited as a structural adhesive in building construction and civil engineering and in industry. For example, a two-component composition of this type, particularly a two-component epoxy resin composition, i.e., in which component K1 comprises a diglycidyl ether, can be used as an adhesive for gluing fiber-reinforced composites. An illustrative example of this is the gluing of carbon fiber plates in the reinforcement of structures, such as bridges.

Furthermore, the two-component compositions of the invention, especially a two-component epoxy resin composition, can be used as a plastic matrix for the production of fiber-reinforced composites. Thus, for example, carbon or glass fibers can be embedded in a two-component composition and can be used in the cured state as a fiber composite, for example, in the form of a plate.

Likewise, for example, woven textiles or scrim can be applied to a structure by means of a two-component composition, particularly by means of a two-component epoxy resin composition, and there together with the structure form a fiber-reinforced composite.

The viscosity of the condensation product of the invention depends greatly on the employed phenolic compound and on the employed polyamine.

Especially suitable condensation products of the invention have a viscosity below 10,000 mPa·s at 25° C. Preferred condensation products of the invention have viscosities in the range between 200 and 7000 mPa·s.

It is clear to the person skilled in the art that in this type of reaction not yet reacted ingredients can be present in the end product in minor amounts.

The condensation products of the invention have no oligomeric compounds.

The present invention will be described in greater detail with use of the following examples.

EXAMPLES

The examples mentioned below serve to illustrate the invention.

1. Preparation Process

A process for preparing condensation products of the invention will be described in greater detail below:
Condensation Product A A 500 mL round vessel is filled with 20 g (0.0473 mol) of Jeffamine® D-400 and 14 g (0.946 mol) of salicylic alcohol and heated under nitrogen on a rotary evaporator. After a homogeneous mixture is obtained (approximately 50° C.), a vacuum is applied (~20 mbar). Next, the temperature is increased to 165° C. The reaction ends after 5 hours affording a brown relatively viscous material ("condensation product A"). An LC-MS analysis shows that the product comprises approximately 45% product of the binuclear aromatic condensation product of the invention, 45% mononuclear aromatic adduct, and 10% unreacted Jeffamine® D-400.

Condensation products B to E were prepared in a similar manner.

TABLE 1

Preparation of condensation products A to E, * = molar ratios of salicylic acid or bis(hydroxymethyl)cresol to Jeffamine D-400 or Jeffamine T-403

|  | MW (g/mol) | A | B | C | D | E |
| --- | --- | --- | --- | --- | --- | --- |
| Salicylic alcohol | 124.14 | 2* | 3* | 2* |  |  |
| Bis(hydroxymethyl)cresol | 168.2 |  |  |  | 2* | 1* |
| Jeffamine D-400 | 400 | 1* |  |  | 1* | 2* |
| Jeffamine T-403 | 438 |  | 1* | 1* |  |  |

2. Application Examples

The samples listed in Table 2 were prepared.

TABLE 2

Compositions and glass transition temperature

|  | Sample 1 | Sample 2 | Sample 3 |
| --- | --- | --- | --- |
| D.E.R. ™ 331 (Dow Chemicals) [g] | 50.0 | 50.0 | 50.0 |
| Condensation product A [g] |  | 41.48 |  |
| Jeffamine ® D-400 (Huntsman) [g] | 26.6 |  | 21.0 |
| Salicylic alcohol (Aldrich) [g] |  |  | 8.5 |
| Tg [° C.] | 39.8 | 38.6 | 19.3 |

The time (t) development of the viscosity (η) was determined with GELNORM-RVN at room temperature in a first practical test. The viscosity is provided here as percentages of the maximum torque. The results are shown in FIG. 1, where (1) stands for Sample 1 (Comparative Example), (2) for Sample 2 (Example of the invention), and (3) for Sample 3 (Comparative Example). A significant acceleration of the curing with condensation product A of the invention from Jeffamine® D-400 and salicylic alcohol in comparison with the use of Jeffamine® D-400 alone or with the use of Jeffamine® D-400 in the presence of free salicylic alcohol.

The results are shown in FIG. 1, where (1) stands for Sample 1 (Comparative Example), (2) for Sample 2 (Example of the Invention), and (3) for Sample 3 (Comparative Example).

As can be derived from FIG. 1, the use (2) according to the invention shows a rapid increase in viscosity, which can be attributed to the progressing curing of bisphenol A diglycidyl ether (BADGE). This increase in viscosity is less evident in (1) and (3).

The present practical test therefore shows that the viscosity of bisphenol A diglycidyl ether in the presence of the condensation product of the invention increases more greatly than with the reference substances (presence of Jeffamine® D-400 alone or in the presence of Jeffamine® D-400 and salicylic alcohol).

These observations are confirmed by the DSC measurements, performed 24 hours after the curing at room temperature.

A Mettler DSC822° device was used for this. 10-20 mg of the compositions was weighed in each case in an aluminum crucible. After the sample was heated from 25° C. to 200° C. in the DSC at a heating rate of 10 K/min, the sample was cooled to 25° C. and then heated to 100° C. at a heating rate of 10 K/min. The glass transition temperature (Tg) was determined with the use of DSC software from the measured DSC curve and listed in Table 2.

The resulting cured epoxy resin, when condensation product A of the invention was used as the hardener (Sample 2), has a glass transition temperature similar to an epoxy resin cured with Jeffamine® D-400 (Sample 1); nevertheless, the curing proceeds much more rapidly.

As is evident from the example according to the invention, the condensation products of the invention are preeminently suitable for accelerating the curing of epoxy resins.

In this regard, the use of phenol as a starting material can be dispensed with, which is advantageous because of the toxicity of free phenol. The use of formaldehyde can also be dispensed with within the scope of the synthesis of the condensation products of the invention. Therefore, the condensation products of the invention can be used as formaldehyde-free accelerators for the curing of epoxy resins.

Because the use of formaldehyde is dispensed with within the scope of the present invention in the synthesis of the condensation products, there is also no undesirable formation of resoles, which lead to an increase in viscosity in the basic synthesis of customary Mannich bases. Thereby, polyamines, which also have a high viscosity per se, can also be used for preparing the condensation products of the invention.

Mixing of the condensation products of the invention with conventional polyamines to adjust the viscosity is also not necessary.

In another practical test, the time (t) development of the viscosity (η) was again determined with GELNORM-RVN at room temperature in condensation products B, C, D, and E.

First a mixture of 0.1 equivalents (H equivalents) of the condensation product with 0.9 equivalents of the starting amine was prepared. In the case of condensation product B, for example, 1 g of condensation product B was combined with 5.37 g of Jeffamine® T-403.

This mixture was then combined in equimolar amounts (in regard to the reactive H groups) with bisphenol A diglycidyl ether (e.g., 13.63 g of bisphenol A diglycidyl ether in the case of condensation product B) and measured in GELNORM-RVN.

A sample consisting solely of the starting amine (Jeffamine® T-403 or Jeffamine® D-400), which was combined in equimolar amounts (in regard to the reactive H groups) with bisphenol A diglycidyl ether, was used as the reference measurement.

Figure 2:
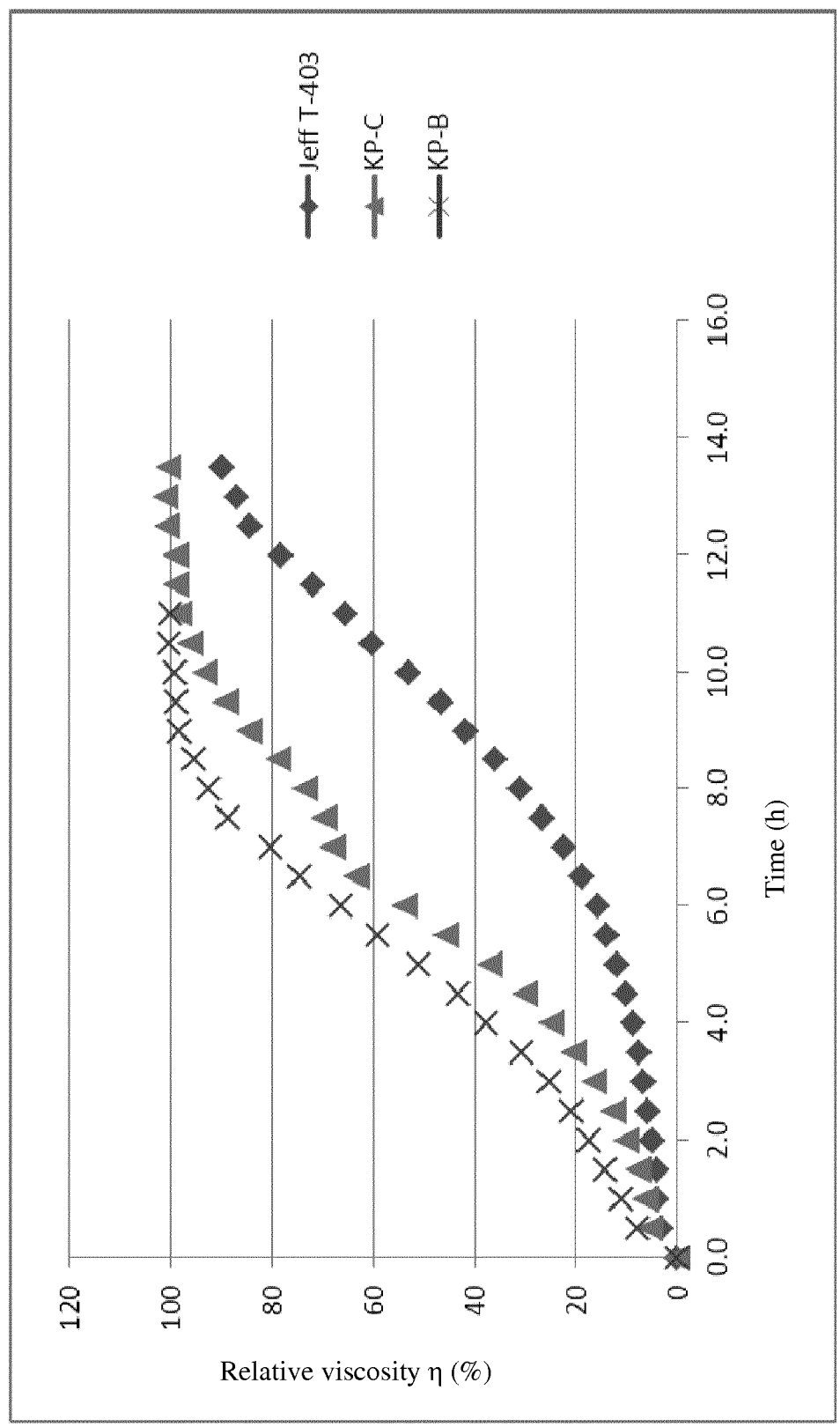
FIG. 2 is a graphical representation illustrating the relative increase in viscosity as a function of the reaction time for condensation products B and C.
Figure 3:
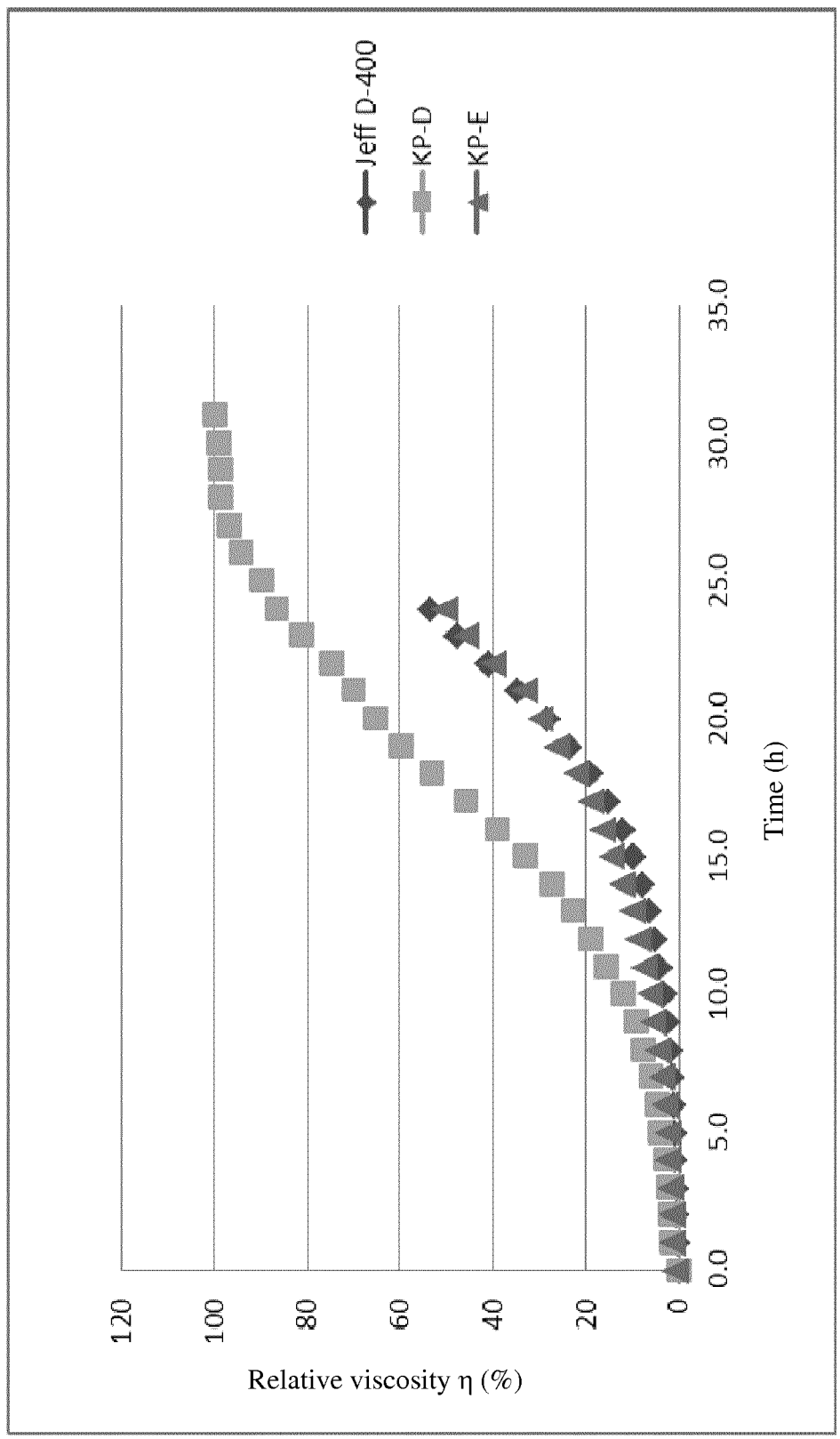
FIG. 3 is a graphical representation illustrating the relative increase in viscosity as a function of the reaction time for condensation products D and E.

The results are shown in FIGS. 2 and 3. FIG. 2 shows the increase in viscosity as a function of the reaction time for condensation products B (KP-B) and C (KP-C) in comparison to a sample consisting solely of the starting amine (Jeff-T403). FIG. 3 shows the increase in viscosity as a function of the reaction time for condensation products D (KP-D) and E (KP-E) in comparison to a sample consisting solely of the starting, amine (Jeff-D400).

It can be seen from the results in FIGS. 2 and 3 that the curing proceeds more rapidly in the case of condensation products comprising a (hydroxymethyl)phenol of the general formula (I) where $R^2$ is hydrogen.

The invention claimed is:

1. An epoxy resin composition comprising an epoxy resin and a condensation product of:
   at least one polyoxyalkylene diamine; and
   at least one (hydroxymethyl)phenol of the general formula (I):

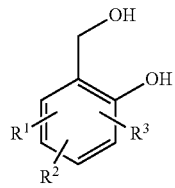

where:
$R^1$ is hydrogen or —CH$_3$;
$R^2$ is hydrogen or —CH$_2$OH; and
$R^3$ is hydrogen or —CH$_3$,
wherein the condensation product is obtained in the absence of formaldehyde.

2. An epoxy resin adhesive comprising the epoxy resin composition of claim 1, wherein the condensation product accelerates the curing of the epoxy resin adhesive and improves the adhesion and/or peel strength of the epoxy resin adhesive.

3. An epoxy resin adhesive comprising the epoxy resin composition of claim 1.

4. An epoxy resin coating comprising the epoxy resin composition of claim 1.

5. The epoxy resin composition according to claim 1, wherein the polyoxyalkylene diamine comprises units based on ethylene oxide, propylene oxide, or ethylene oxide and propylene oxide.

6. The epoxy resin composition according to claim 1, wherein the polyoxyalkylene diamine corresponds to the general structure (II):

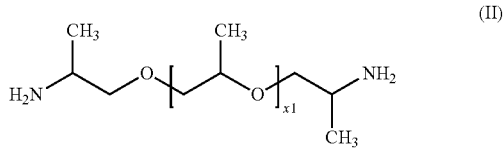

wherein X1 stands for a value of 2 to 70.

7. The epoxy resin composition according to claim 1, wherein the polyoxyalkylene diamine corresponds to the general structure (III):

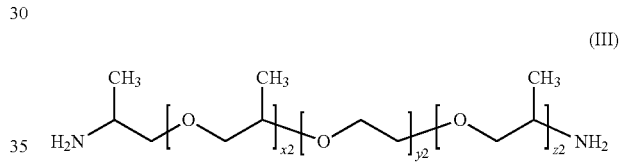

wherein x2, y2, and z2 have the following meaning:
y2 is 2 to 40; and
x2+z2 is 1 to 7.

8. The epoxy resin composition according to claim 1, wherein the polyoxyalkylene diamine has a molecular weight of 220 to 10,000 g/mol.

* * * * *